(12) United States Patent
Honda et al.

(10) Patent No.: US 10,696,701 B2
(45) Date of Patent: Jun. 30, 2020

(54) BIS(6-METHYL-3-SULPHOPHENYL) PHENYLPHOSPHINE, AMMONIUM SALT THEREOF, AND METHOD FOR PRODUCING SAME

(71) Applicants: KURARAY CO., LTD., Kurashiki-shi (JP); HOKKO CHEMICAL INDUSTRY CO., LTD., Chuo-ku (JP)

(72) Inventors: Eriko Honda, Okayama (JP); Tatsuya Yoshikawa, Kamisu (JP); Tomoaki Tsuji, Kamisu (JP); Hitoshi Koizumi, Hiratsuka (JP); Kyoko Sugita, Atsugi (JP); Nobumichi Kumamoto, Atsugi (JP)

(73) Assignees: KURARAY CO., LTD., Kurashiki-shi (JP); HOKKO CHEMICAL INDUSTRY CO., LTD., Chuo-ku (JP)

( * ) Notice: Subject to any disclaimer, the term of this patent is extended or adjusted under 35 U.S.C. 154(b) by 219 days.

(21) Appl. No.: 15/872,550

(22) Filed: Jan. 16, 2018

(65) Prior Publication Data

US 2018/0141967 A1 May 24, 2018

Related U.S. Application Data

(63) Continuation of application No. 14/779,407, filed as application No. PCT/JP2014/058668 on Mar. 26, 2014, now abandoned.

(30) Foreign Application Priority Data

Mar. 27, 2013 (JP) ................. 2013-067281

(51) Int. Cl.
| | |
|---|---|
| *C07C 29/36* | (2006.01) |
| *C07F 9/50* | (2006.01) |
| *C07C 211/05* | (2006.01) |
| *C07C 211/07* | (2006.01) |
| *C07C 211/08* | (2006.01) |
| *B01J 31/02* | (2006.01) |

(52) U.S. Cl.
CPC ......... *C07F 9/5022* (2013.01); *B01J 31/0225* (2013.01); *B01J 31/0267* (2013.01); *B01J 31/0271* (2013.01); *C07C 211/05* (2013.01); *C07C 211/07* (2013.01); *C07C 211/08* (2013.01); *B01J 2231/20* (2013.01)

(58) Field of Classification Search
None
See application file for complete search history.

(56) References Cited

U.S. PATENT DOCUMENTS

| 4,716,250 A | 12/1987 | Abatjoglou et al. |
| 5,057,631 A | 10/1991 | Tokitoh et al. |
| 5,114,473 A | 5/1992 | Abatjoglou et al. |
| 5,908,805 A | 6/1999 | Huser et al. |
| 2002/0183196 A1 | 12/2002 | Yada et al. |
| 2004/0260118 A1 | 12/2004 | Yada et al. |
| 2016/0046549 A1 | 2/2016 | Yoshikawa et al. |

FOREIGN PATENT DOCUMENTS

| CN | 87105466 A | 2/1988 |
| CN | 1206357 A | 1/1999 |
| CN | 1699382 A | 11/2005 |
| EP | 2 980 055 A1 | 2/2016 |
| JP | 63 88150 | 4/1988 |
| JP | 64 25739 | 1/1989 |
| JP | 3 232831 | 10/1991 |
| JP | 6 321828 | 11/1994 |
| JP | 8 501800 | 2/1996 |
| JP | 8 176167 | 7/1996 |
| JP | 2002 371088 | 12/2002 |
| JP | 2003 171388 | 6/2003 |
| WO | 95/30635 A1 | 11/1995 |
| WO | 95 30636 | 11/1995 |

OTHER PUBLICATIONS

Gulyas et al. "Preparation of New Sulfonated Triarylphosphanes: Control of the Selectivity by Stuctural Assistance", Eur. J. Org. Chem. 2003, pp. 2775-2781.
Gulyas et al., "A direct approach to selective sulfonation of triarylphospines", Tetrahedron Letters, vol. 43, No. 14, (2002), pp. 2543-2546.
Monflier et al., "Palladium catalyzed telomerization of butadiene with water in a two phase system: drastic effect of the amine structure on the rate and selectivity", Journal of Molecular Catalyasis A: Chemical, vol. 97. (1995), pp. 29-33.
Thorpe et al., "A practical synthesis of a disulfonated phosphine and its application to biphasic catalysis", Tetrahedron Letters. vol. 41, (2000). pp. 4503-4505.
Bhanage et al., "Selectivity in Sulfonation of Triphenyl Phosphine", Organic Process Research & Development, vol. 4, (2000), pp. 342-345.
Ferreira et al., "Biphasic Aqueous Organometallic Catalysis Promoted by Cyclodextrins: How to Design the Water-Soluble Phenylphosphane to Avoid Interaction with Cyclodextrin", Advanced Synthesis & Catalysis, vol. 350, (2008), pp. 609-618.
Extended European Search Report dated Jul. 13, 2016 in Patent Application No. 14773289.5.

(Continued)

*Primary Examiner* — Yun Qian
(74) *Attorney, Agent, or Firm* — Oblon, McClelland, Maier & Neustadt, L.L.P.

(57) ABSTRACT

Provided are a water-soluble triarylphosphine for a palladium catalyst, which has high selectivity in a telomerization reaction and can be recovered with efficiency, an ammonium salt thereof, and a method for efficiently producing the same. Specifically, provided are bis(6-methyl-3-sulphophenyl) phenylphosphine; a bis(6-methyl-3-sulphonatopheyl)phenylphosphine diammonium salt obtained by reacting the phosphine with a tertiary amine having a total of 3 to 27 carbon atoms in groups bonded to one nitrogen atom; and a method for producing the same.

10 Claims, No Drawings

(56) References Cited

OTHER PUBLICATIONS

Combined Chinese Office Action and Search Report dated Jul. 15. 2016 in Patent Application No. 20140017408.8 (with English language translation of categories of cited documents).
International Search Report dated Jul. 1, 2014 in PCT/JP14/058668 Filed Mar. 26, 2014.

BIS(6-METHYL-3-SULPHOPHENYL) PHENYLPHOSPHINE, AMMONIUM SALT THEREOF, AND METHOD FOR PRODUCING SAME

CROSS REFERENCE TO RELATED APPLICATIONS

The present application is a Continuation of U.S. application Ser. No. 14/779,407, filed on Sep. 23, 2015, which was a 35 U.S.C. § 371 national stage patent application of International patent application PCT/JP2014/058668, filed on Mar. 26, 2014, the text of which is incorporated by reference, and claims the benefit of the filing date of Japanese application no. 2013-067281, filed on Mar. 27, 2013, the text of which is also incorporated by reference.

TECHNICAL FIELD

The present invention relates to bis(6-methyl-3-sulphophenyl)phenylphosphine, an ammonium salt thereof, and a method for producing the same.

BACKGROUND ART

A palladium catalyst comprised of a phosphorous compound and a palladium compound is useful as a catalyst for a telomerization reaction between two conjugated alkadiene molecules and a nucleophilic reactant. Specifically, it is useful as a catalyst for production of 2,7-octadien-1-ol by reacting two butadiene molecules with one water molecule in the presence of carbon dioxide and a tertiary amine to perform a telomerization reaction. 7-Octenal can be derived from 2,7-octadien-1-ol thus obtained by an isomerization reaction and 1,9-nonanedial can be derived from 7-octenal by a hydroformylation reaction. From the viewpoint that 1,9-nonanediamine which is useful as a raw material for a monomer for a polymer can be derived from 1,9-nonanedial by a reductive amination reaction, the 2,7-octadien-1-ol is of a high industrial value, and it is therefore important to develop a catalyst advantageous for the production thereof.

In order to produce 2,7-octadien-1-ol in an industrially advantageous manner, it is preferable to recover palladium as a noble metal in the telomerization reaction and reuse it in the reaction. As such a method for producing 2,7-octadien-1-ol, there are two methods using a telomerization reaction, as followings:

(A) a method for producing 2,7-octadien-1-ol, in which butadiene and water are subjected to a telomerization reaction in the presence of a palladium catalyst comprised of a palladium compound and a water-soluble phosphine in an aqueous sulfolane solution including a carbonate of a tertiary amine and a bicarbonate of a tertiary amine to generate 2,7-octadien-1-ol, in which at least part of the reaction mixed liquid is extracted with a saturated aliphatic hydrocarbon or the like to separate out the 2,7-octadien-1-ol by extraction, and at least a part of the sulfolane eluent including the palladium catalyst is recycled and used in the reaction (see PTLs 1 to 3), and (B) a method for producing 2,7-octadien-1-ol, in which a tertiary amine having a function as a surfactant capable of compensating for a low reaction rate due to low solubility of butadiene in water coexists therewith in a two-phase system including an aqueous phase having a palladium catalyst comprised of a palladium compound and a water-soluble phosphorus-containing compound dissolved in water and an organic phase which is butadiene, and then butadiene and water are subjected to a telomerization reaction (see PTL 4 and NPL 1).

In the method (A), 2,7-octadien-1-ol is extracted by adding a saturated aliphatic hydrocarbon to a telomerization reaction liquid, and it is thus necessary to install equipment for distillation and recovery of the saturated aliphatic hydrocarbon, which results in an increase in cost burden associated with the equipment. Further, sulfolane is more expensive than ordinary hydrocarbon-based solvents, such as hexane, and accordingly, it is necessary to recover the sulfolane by subjecting the 2,7-octadien-1-ol phase obtained by extraction to washing with water, or the like. In addition, since sulfolane is a sulphur atom-containing substance, in a case of incineration disposal of sulfolane, an incinerator having desulphurization equipment is required. Therefore, there is a demand for a method for conveniently recovering most of a palladium catalyst after a telomerization reaction while not using sulfolane in the telomerization reaction.

In the method (B), dimethyldodecylamine, for example, is used as a tertiary amine. Since the dimethyldodecylamine has a function as a surfactant, complicated operations such as multiple extraction and recovery, or distillation and separation are required so as to increase the recovery of a tertiary amine. Further, according to Examples, it can be said that the method (B) is a method having low selectivity for 2,7-octadien-1-ol. Therefore, there is also a demand for a method in which the tertiary amine to be easily recovered can be used, and the selectivity for 2,7-octadien-1-ol is high.

Moreover, as a method for producing a water-soluble triarylphosphine which can be used in a telomerization reaction, the following methods are known:

(1) a method for producing a bis(3-sulphonatophenyl)phenylphosphine disodium salt, by dissolving triphenylphosphine in sulphuric acid, and then reacting the solution with sulphur trioxide in fuming sulphuric acid (see NPLs 2 and 3), (2) a method for producing a bis(3-sulphonatophenyl)phenylphosphine disodium salt by sulphonation of triphenylphosphine using an anhydrous mixture of sulphuric acid and orthoboric acid (see PTL 5), (3) a method in which triarylphosphine having an electron donating group such as a methyl group and a methoxy group in an aromatic ring is reacted with sulphur trioxide in the presence of sulphuric acid (see NPL 4), and (4) a method in which triarylphosphine having an electron donating group such as a methyl group and a methoxy group in each of three aromatic rings is reacted with sulphur trioxide in the presence of sulphuric acid (see NPL 5).

In the case of using the alkali metal salt of a triarylphosphine having a sulphonate group, obtained by these methods, in a telomerization reaction, there is a problem in that inorganic salts such as hydrogen carbonate of an alkali metal are accumulated in the reaction system, thus blocking pipes. It is known that as a method to avoid this problem, it is preferable to use an ammonium salt obtained by reacting a triarylphosphine having a sulphonate group with a tertiary amine as a catalyst for a telomerization reaction (see PTL 6).

In the method (1) for producing a water-soluble triarylphosphine, a bis(3-sulphonatophenyl)phenylphosphine disodium salt can be produced by sulphonating triphenylphosphine having a benzene ring as an equivalent aromatic ring relative to one phosphorus atom bonded thereto with sulphur trioxide, followed by neutralization with sodium hydroxide, but the yield is as low as 60%. This is mainly caused by by-production of a tris(3-sulphonatophenyl)phosphine trisodium salt, indicating that it is difficult to selectively introduce only "two" sulpho groups with respect to the equivalent aromatic ring.

The method (2) for producing a water-soluble triarylphosphine is a method in which orthoboric acid is used instead of sulphur trioxide during a sulphonation reaction. The bis(3-sulphonatophenyl)phenylphosphine disodium salt is acquired with a yield of 94%, but in order to remove boric acid completely, toluene and triisooctylamine are added to a sulphonation reaction liquid once to cause a desired amine salt to be present in an organic phase, the organic phase is sufficiently washed with water, and the aqueous phase obtained by adding an aqueous sodium hydroxide solution to the washed organic phase is neutralized with sulphuric acid, and then concentrated. Then, methanol is added thereto to obtain a supernatant, from which methanol is removed, thereby acquiring a bis(3-sulphonatophenyl)phenylphosphine disodium salt. Although the yield is high, it is necessary to repeat washing to remove boric acid. Therefore, this method is difficult to carry out industrially.

The method (3) for producing a water-soluble triarylphosphine is a method in which a triarylphosphine in which an electron donating group such as a methyl group and a methoxy group is introduced in advance to an aromatic ring is reacted with sulphur trioxide in the presence of sulphuric acid. Bis(4-methoxyphenyl)phenylphosphine having a non-equivalent aromatic ring, or the like is used as a raw material to acquire bis(4-methoxy-3-sulphonatophenyl)phenylphosphine disodium salt with a yield of 85%. Further, it can be shown that in the method (4) for producing a water-soluble triarylphosphine, a bis(6-methyl-3-sulphonatophenyl)(3-sulphonatophenyl)phosphine trisodium salt can be produced with a yield of 21% from bis(2-methylphenyl)phenylphosphine. However, from the viewpoint that the bis(2-methylphenyl)phenylphosphine used in the present invention has a small number of substituents such as a methyl group, as compared with bis(2,4-dimethylphenyl)phenylphosphine, the number of sulpho groups or sulphonate groups introduced tends to be 3, and therefore, there is a concern that the yield of a desired bis(6-methyl-3-sulphophenyl)phenylphosphine, and in addition, the yield of the bis(6-methyl-3-sulphonatophenyl)phenylphosphine diammonium salt will be lowered.

As a method for producing an ammonium salt of a triarylphosphine having a sulphonate group, methods in which for an alkali metal salt of a triarylphosphine having a sulphonate group is used as a raw material, a counter-cation is converted into a desired ammonium salt by an ion exchange process in the following manner are known. The methods are as follows:

a method in which sulphuric acid is added to an aqueous solution of a diphenyl(3-sulphonatophenyl)phosphine sodium salt, 4-methyl-2-pentanone is then added thereto, and triethylamine is added to the obtained organic phase, thereby precipitating a solid-state diphenyl(3-sulphonatophenyl)phosphine triethylammonium salt (see PTL 6); and a method in which a diphenyl(3-sulphonatophenyl)phosphine sodium salt is pressurized with carbon dioxide in the presence of triethylamine, ethanol, and 2-propanol to acquire a desired product from a filtrate of the reaction liquid (see PTL 7).

CITATION LIST

Patent Literature

[PTL 1] JP-A-64-25739
[PTL 2] JP-A-3-232831
[PTL 3] JP-A-6-321828
[PTL 4] JP-A-8-501800
[PTL 5] JP-A-8-176167
[PTL 6] JP-A-2002-371088
[PTL 7] JP-A-2003-171388

Non Patent Literature

[NPL 1] Journal of Molecular Catalysis A: Chemical, vol. 97, 1995, pp. 29 to 33
[NPL 2] Tetrahedron Letters, 2000, vol. 41, pp. 4503 to 4505
[NPL 3] Organic Process Research & Development, 2000, vol. 4, pp. 342 to 345
[NPL 4] Tetrahedron Letters, vol. 43, 20002, pp. 2543 to 2546
[NPL 5] Advanced Synthesis & Catalysis, 2008, vol. 350, pp. 609 to 618

SUMMARY OF INVENTION

Technical Problem

In the ion exchange method described in PTL 6, according to the investigations of the present inventors, bis(6-methyl-3-sulphophenyl)phenylphosphine was insufficiently extracted with an acyclic ketone solvent, and therefore, the yield was as low as 30% or less.

In the ion exchange method described in PTL 7, according to the investigations of the present inventors, when the same operation was carried out using a bis(6-methyl-3-sulphonatophenyl)phenylphosphine disodium salt, the ion exchange rate of the counter-cation was as low as 20% or less.

Therefore, it is an object of the present invention to provide a water-soluble triarylphosphine for a palladium catalyst, which has high selectivity in a telomerization reaction and is easily recovered with efficiency, and a method for efficiently producing the same efficiently.

Solution to Problem

The present inventors have conducted extensive studies, and as a result, they have found that the selectivity for desired products is increased in a telomerization reaction of two molecules of an alkadiene such as butadiene with a nucleophilic reactant such as water by using a palladium catalyst comprised of a specific ammonium salt of bis(6-methyl-3-sulphophenyl)phenylphosphine and a palladium compound. Further, they have also found that in the case of using the palladium catalyst in a telomerization reaction, products can be extracted from the organic phase by adding an organic solvent having a specific dielectric constant to the obtained telomerization reaction liquid, while recovery of the palladium catalyst from the aqueous phase can be carried out with high yield, thereby completing the present invention.

That is, the present invention relates to [1] to [2] below.
[1] Bis(6-methyl-sulphophenyl)phenylphosphine.
[2] A bis(6-methyl-3-sulphonatophenyl)phenylphosphine diammonium salt obtained by reacting the bis(6-methyl-3-sulphonatophenyl)phenylphosphine according to [1] with a tertiary amine having a total of 3 to 27 carbon atoms in groups bonded to one nitrogen atom.
[3] The bis(6-methyl-3-sulphonatophenyl)phenylphosphine diammonium salt according to [2], wherein the tertiary amine is trimethylamine, triethylamine, tripropylamine, triisopropylamine, tributylamine, triisobutylamine, tri-s-butylamine, tri-t-butylamine, tripentylamine, triisopentylamine, trineopentylamine, trihexylamine, triheptylamine, trioctylamine, triphenylamine, tribenzylamine, N,N-dimethylethylamine, N,N-dimethylpropylamine, N,N-dimethylisopropylamine, N,N-dimethylbutylamine, N,N-dimethylisobutylamine, N,N-dimethyl-s-butylamine, N,N-dimethyl-t-butylamine, N,N-dimethylbentylamine, N,N-dimethylisopentylamine, N,N-dimethylneopentylamine, N,N-dimethylhexylamine, N,N-dimethylheptylamine, N,N-dimethyloctylamine, N,N-dimethylnonylamine, N,N-dimethyldecylamine, N,N-dimethylundecylamine, N,N-dimethyldodecylamine, N,N-dimethylphenylamine, N,N-dimethylbenzylamine, N,N-diethylmonomethylamine, N,N-dipropylmonomethylamine, N,N-diisopropylmonomethylamine, N,N-dibutylmonomethylamine, N,N-diisobutylmonomethylamine, N,N-di-s-butylmonomethylamine, N,N-di-t-butylmonomethylamine, N,N-dipentylmonomethylamine, N,N-diisopentylmonomethylamine, N,N-dineopentylmonomethylamine, N,N-dihexylmonomethylamine, N,N-diheptylmonomethylamine, N,N-dioctylmonomethylamine, N,N-dinonylmonomethylamine, N,N-didecylmonomethylamine, N,N-diundecylmonomethylamine, N,N-didodecylmonomethylamine, N,N-diphenylmonomethylamine, N,N-dibenzylmonomethylamine, N,N-dipropylmonoethylamine, N,N-diisopropylmonoethylamine, N,N-dibutylmonoethylamine, N,N-diisobutylmonoethylamine, N,N-di-s-butylmonoethylamine, N,N-di-t-butylmonoethylamine, N,N-dipentylmonoethylamine, N,N-diisopentylmonoethylamine, N,N-dineopentylmonoethylamine, N,N-dihexylmonoethylamine, N,N-diheptylmonoethylamine, N,N-dioctylmonoethylamine, N,N-dinonylmonoethylamine, N,N-didecylmonoethylamine, N,N-diumdecylmonoethylamine, N,N-didodecylmonoethylamine, N,N-diphenylmonoethylamine, N,N-dibenzylmonoethylamine, or trinonylamine.

[4] A mixture containing 90% by mole or more of Bis(6-methyl-3-sulphophenyl)phenylphosphine, and 10% by mole or less of (6-methyl-3-sulphophenyl)(2-methylphenyl)phenylphosphine.

[5] A mixture containing 90% by mole or more of a bis(6-methyl-3-sulphonatophenyl)phenylphosphine diammonium salt obtained by reacting the mixture according to [4] with a tertiary amine having a total of 3 to 27 carbon atoms in groups bonded to one nitrogen atom.

[6] A method for producing bis(6-methyl-3-sulphophenyl) phenylphosphine, having: a step of reacting 2.5 moles to 4.5 moles of sulphur trioxide with 1 mole of bis(2-methylphenyl)phenylphosphine in the presence of concentrated sulphuric acid to obtain a sulphonation reaction liquid, and diluting the obtained sulphonation reaction liquid with water to obtain a diluted liquid; a step of neutralizing the diluted liquid with an alkali metal hydroxide; and a step of bringing the aqueous solution obtained in the neutralization step into contact with a strongly acidic cation exchange resin.

[7] A method for producing a bis(6-methyl-3-sulphonatophenyl)phenylphosphine diammonium salt by reacting bis(6-methyl-3-sulphophenyl)phenylphosphine with a tertiary amine having a total of 3 to 27 carbon atoms in groups bonded to one nitrogen atom.

Advantageous Effects of Invention

High selectivity in a telomerization reaction can be accomplished by using a water-soluble triarylphosphine for a palladium catalyst of the present invention, and the palladium catalyst after use can be efficiently recovered. Further, a water-soluble triarylphosphine, which will be a raw material for a palladium catalyst, can be selectively produced by the production method of the present invention.

DESCRIPTION OF EMBODIMENTS

First, in the present specification, the restrictive wording with "being preferable" can be arbitrarily adopted, and a combination of restrictive wordings with "being preferable" can be said to be more preferred.

The present invention provides bis(6-methyl-3-sulphophenyl)phenylphosphine and an ammonium salt thereof. The ammonium salt thereof is more specifically a bis(6-methyl-3-sulphonatophenyl)phenylphosphine diammonium salt.

These can be produced efficiently by the following steps, but the invention is not particularly limited to the following steps.

[1. Sulphonation Step]

A step of reacting 2.5 moles to 4.5 moles of sulphur trioxide with 1 mole of bis(2-methylphenyl)phenylphosphine in the presence of concentrated sulphuric acid to obtain a sulphonation reaction liquid, and diluting the obtained sulphonation reaction liquid with water to obtain a diluted liquid is included.

[2. Neutralization Step]

A step of neutralizing the diluted liquid with an alkali metal hydroxide to obtain an aqueous solution including a bis(6-methyl-3-sulphonatophenyl)phenylphosphine dialkali metal salt.

[3. Ion Exchange Step]

A step of bringing the aqueous solution obtained in the neutralization step into contact with a strongly acidic cation exchange resin to for bis(6-methyl-3-sulphophenyl)phenylphosphine.

The bis(6-methyl-3-sulphophenyl)phenylphosphine can be produced by the steps hitherto described. Further, for the production of a bis(6-methyl-3-sulphonatophenyl)phenylphosphine diammonium salt, the following steps are further required.

[4. Ammonium Salt Forming Step]

A step of reacting bis(6-methyl-3-sulphophenyl)phenylphosphine with a tertiary amine having a total of 3 27 carbon atoms in groups bonded to one nitrogen atom to form a bis(6-methyl-3-sulphonatophenyl)phenylphosphine diammonium salt.

Furthermore, the steps will be described in detail below, but from the viewpoint that the phosphine compound is easily oxidized by oxygen, although not being clearly described, operations in the steps are carried out in an inert gas atmosphere in principle. Furthermore, from the same viewpoint, in the case of using a solvent, it is preferable to use a solvent having dissolved oxygen included in the solvent is purged with an inert gas. Examples of the inert gas include nitrogen, helium, and argon, and from the viewpoint of high industrial availability, it is preferable to use nitrogen gases.

[1. Sulphonation Step]

The method for producing bis(2-methylphenyl)phenylphosphine is not particularly limited, and the bis(2-methylphenyl)phenylphosphine can be produced according to a known method. For example, a reaction of dichlorophenyl phosphine with a Grignard reagent obtained from 2-bromotoluene (see Journal of Organic Chemistry, 1978, vol. 43, pp. 2941 to 2956) and the like are known.

The operation sequence in the reaction of bis(2-methylphenyl)phenylphosphine with sulphur trioxide in the presence of concentrated sulphuric acid is not particularly limited, but for example, bis(2-methylphenyl)phenylphosphine can be sulphonated by dissolving bis(2-methylphenyl)phenylphosphine in concentrated sulphuric acid, followed by reaction with sulphur trioxide.

Furthermore, sulphonation can also be carried out by the reaction with orthoboric acid instead of sulphur trioxide. According to the findings of the present inventors, in the case of using orthoboric acid, from the viewpoint that the removal of orthoboric acid from the sulphonation reaction liquid is complicated, it is preferable to use sulphur trioxide, and it is more preferable to use fuming sulphuric acid including sulphur trioxide and sulphuric acid.

The sulphonation step can be carried out using a continuous stirred tank reactor equipped with a jacket. The continuous stirred tank reactor as mentioned herein is a reactor designed such that raw materials supplied to the reactor are mixed in a substantially homogeneous dispersion state without any delay.

The material for the reactor is preferably stainless steel, Hastelloy C, titanium, or the like, and further, as a material for an inner wall of a reactor, a glass-lined material may be used. From the viewpoint of avoiding the incorporation of metal ions originating from the reactor into a desired product, it is preferable to use glass-lined materials for the inner wall. Further, the glass lining process is a method in which two materials, a metal and glass, are fused to perform surface modification of the metal.

The sulphonation step can be carried out in any of a batch mode (including a semi-continuous mode) and a flow and continuous mode. In some cases, it can also be carried out in the flow and continuous mode by connecting two or three continuous stirred tank reactors in series. From the viewpoint that simplification of equipment results from dilution of a sulphonation reaction liquid with water as described later and the subsequent neutralization step, both carried out in one reaction tank, it is preferable to carry out the process in a batch mode (including a semi-continuous mode).

Concentrated sulphuric acid serves to dissolve bis(2-methylphenyl)phenylphosphine. As the concentrated sulphuric acid, one having a high content of sulphuric acid is preferred, and from the viewpoint of industrial availability, one having a concentration of 96% by mass or more is more preferably used. A higher content of sulphuric acid in concentrated sulphuric acid is preferable since it can inhibit the hydrolysis of sulphur trioxide in fuming sulphuric acid. From the viewpoint that fuming sulphuric acid is more expensive than sulphuric acid, it is economically preferable to inhibit the hydrolysis of sulphur trioxide.

Since concentrated sulphuric acid used for sulphonation is generally subjected to a disposal treatment by forming a sulphuric acid alkali metal salt by neutralization with an alkali metal hydroxide or the like, production conditions for reducing the amount of sulphuric acid used are preferred. From this view point, the amount of sulphuric acid used is preferably about an amount which allows bis(2-methylphenyl)phenylphosphine to be dissolved, and more preferably an amount which adjusts the amount of bis(2-methylphenyl)phenylphosphine to be from 20% by mass to 70% by mass. Within this range, the amount of sulphuric acid to be disposed of can be reduced, it becomes possible to perform a reaction with sulphur trioxide in a sufficiently mixed state due to low viscosity of the prepared mixed solution, and in addition, the yield of the desired product is enhanced.

The temperature at a time of preparation of a concentrated sulphuric acid solution of bis(2-methylphenyl)phenylphosphine is preferably from 0° C. to 100° C., and more preferably from 20° C. to 40° C. Within this range, the oxidation reaction of bis(2-methylphenyl)phenylphosphine does not proceed, it becomes possible to perform a reaction with sulphur trioxide in a sufficiently mixed state due to low viscosity of the prepared mixed solution, and in addition, the yield of the desired product is enhanced.

Sulfur trioxide is preferably used for the reaction in the form of a fuming sulphuric acid in which sulphur trioxide is dissolved in sulphuric acid. The concentration of sulphur trioxide in fuming sulphuric acid is preferably from 10% by mass to 60% by mass, and more preferably from 20% by mass to 50% by mass. Within this range, the amount of sulphuric acid practically used can be reduced, and the time required for the sulphonation step can be shortened due to a fact that the sulphur trioxide concentration in the reaction system can be maintained at a certain level or higher.

The amount of sulphur trioxide used is preferably from 2.5 moles to 4.5 moles, and more preferably form 3.0 moles to 4.0 moles, with respect to one mole of phosphorous atoms contained in bis(2-methylphenyl)phenylphosphine. Within this range, the yield of the desired product is high. Further, the numerical value range is a numerical value not considering the consumption by hydrolysis. In the case where consumption by hydrolysis is considered, it is preferable to increase the amount of sulphur trioxide used according to the amount.

The reaction temperature for the sulphonation step is preferably from 0° C. to 100° C., more preferably from 10° C. to 50° C., and still more preferably from 20° C. to 50° C. Within this range, even in the state where the reaction time is short, the yield of a desired product is high.

It is preferable to add fuming sulphuric acid to a concentrated sulphuric acid solution of bis(2-methylphenyl)phenylphosphine slowly, and the time taken for the addition is preferably from 0.25 hours to 5 hours, and more preferably from 0.5 hours to 3 hours. Within this range, the reaction time is not too long, and the yield of a desired product is high. Further, it is preferable that after the addition of fuming sulphuric acid, the flow path of the fuming sulphuric acid is washed with concentrated sulphuric acid, and a washing liquid thus obtained is mixed with the reaction solution.

The reaction time after the completion of addition of fuming sulphuric acid is preferably from 2 hours to 20 hours, and more preferably from 2 hours to 8 hours. In the case of this range, the yield of a desired product is high.

(Water Dilution Operation)

Unreacted sulphur trioxide can be hydrolyzed by diluting the sulphonation reaction liquid obtained by the operation above with water, whereby it is possible to stop the sulphonation reaction.

Furthermore, water used for the dilution serves to remove the dilution heat of concentrated sulphuric acid and the hydrolysis reaction heat of sulphur trioxide, and also serves as a solvent in the neutralization step of the next step.

The temperature of water used for dilution may be any temperature at which water does not freeze, and it is preferably from 1° C. to 40° C., and more preferably from 2° C. to 25° C. Among the temperatures in this range, a lower temperature is preferred since heat can be efficiently removed.

The amount of water used may be at least any amount in which unreacted sulphur trioxide can be hydrolyzed, but from the viewpoint of control of the temperature in the neutralization step as described later, it is from 1 time to 20 times by mass that of the sulphonation reaction liquid. Within this range, heat removal is easy and the amount of waste water in the neutralization step as described later can be reduced.

The liquid temperature at the time of dilution with water is preferably from 0° C. to 100° C., and more preferably from 1° C. to 40° C. Within this range, operations such as lowering the temperature of the liquid at a time of starting the neutralization step are not required, and thus, the productivity can be improved.

[2. Neutralization Step]

In the neutralization step, the reactor used in the sulphonation step is used as it is, and further, it is preferable to continuously carry out the step in a batch mode (including a semi-continuous mode) from the viewpoint of simplification of facilities.

Examples of the alkali metal hydroxide used in the neutralization step include lithium hydroxide, sodium hydroxide, and potassium hydroxide. Among these, potassium hydroxide and sodium hydroxide are preferred, and sodium hydroxide is more preferred.

By using the alkali metal hydroxide, a high ion exchange rate from bis(6-methyl-3-sulphonatophenyl)phenylphosphine dialkali metal salt to bis(6-methyl-3-sulphophenyl)phenylphosphine with a strongly acidic cation exchange resin can be accomplished.

The alkali metal hydroxide may be used in the form of a solid and may be used as an aqueous solution. However, from the viewpoints of avoiding local heat generation at a time of neutralization and increasing the heat removal efficiency, the alkali metal hydroxide is preferably used as an aqueous solution. The concentration of the aqueous alkali metal hydroxide solution is not particularly limited, and the aqueous alkali metal hydroxide solution is preferably used at a concentration of 10% by mass to 50% by mass, and more preferably used at a concentration of 20% by mass to 40% by mass. Within this range, the liquid amount after the neutralization is low, and thus, the amount of waste water can be reduced. Further, it is preferable that the aqueous alkali metal hydroxide solution is slowly added to the sulphonation reaction liquid obtained in the sulphonation step, and in some cases, the aqueous alkali metal hydroxide solution can be added in several separate portions. Further, after using the aqueous alkali metal hydroxide solution in this concentration range, aqueous alkali metal hydroxide solutions having different concentrations, for example, an aqueous alkali metal hydroxide solution (usually an aqueous alkali metal hydroxide solution having a low concentration) having a concentration outside of the range may be used later.

The amount of alkali metal hydroxide used is not particularly limited as long as it can neutralize sulphuric acid and bis(6-methyl-3-sulphophenyl)phenylphosphine, and it is preferably an amount such that the pH of the aqueous solution at 25° C. after the completion of neutralization is preferably from 7.0 to 9.5, and more preferably from 7.5 to 8.5. Within this range, most of a sulphuric acid can be introduced to a sulphuric acid alkali metal salt. Further, excess alkali metal hydroxide can be converted into water in the ion exchange step as described later.

The neutralization temperature is not particularly limited, and usually, it is preferably from 0° C. to 40° C., and more preferably from 1° C. to 25° C. in order to promote desirable precipitation of alkali metal sulphate. When the neutralization temperature is 0° C. or higher, the amount of energy consumed, relevant to cooling, can be reduced, which is thus preferable. Further, when the neutralization temperature is 40° C. or lower, precipitation of the alkali metal sulphate during the transportation of the liquid can be inhibited, and therefore, there is no concern about pipes becoming blocked.

The time required for the neutralization is any time as long as it is in a range suitable for the heat removal ability of a reactor used. Specifically, the time is preferably from 0.5 hours to 20 hours, and more preferably from 2 hours to 5 hours. When the time is 0.5 hours or longer, it is possible to remove neutralization heat efficiently. As a result, it is economically advantageous since it is not necessary to use a continuous stirred tank with high efficiency in heat removal. When the time is 20 hours or shorter, the increase in the amount of energy consumed for maintenance of the set temperature can be inhibited, which is thus preferable.

The aqueous solution formed by the neutralization in the present step (hereinafter referred to as a neutralized liquid) has bis(6-methyl-3-sulphonatophenyl)phenylphosphine dialkali metal salt and an alkali metal sulphate as a main component.

The aqueous solution formed by the neutralization in the present step (hereinafter referred to as a neutralize liquid) has bis(6-methyl-3-sulphonatophenyl)phenylphosphine dialkali metal salt and an alkali metal sulphate as a main component.

The solubility in an alcohol such as methanol, ethanol, and 1-propanol, of the bis(6-methyl-3-sulphonatophenyl)phenylphosphine dialkali metal salt, is higher than that of the alkali metal sulphate, and thus, by using the difference in the solubility, the alkali metal sulphate can be separated out. Although it is possible to precipitate the alkali metal sulphate by directly adding the alcohol to the neutralized liquid, it is preferable to evaporate as much water as possible from the neutralized liquid in advance, and it is more preferable to evaporate 90% by mass to 98% by mass of water in the neutralized liquid, from the viewpoints of reducing the amount of the alcohol used and inhibiting the incorporation of the alkali metal sulphate into a desired product. In this manner, an approach in which the alcohol is added to a concentrate obtained by evaporating water to separate out the alkali metal sulphate is preferred.

Examples of the alcohol include methanol, ethanol, and 1-propanol, and from the viewpoint of reducing the amount of the alcohol, it is preferable to use methanol.

The amount of the alcohol used for separating out the alkali metal sulphate is not particularly limited, and is preferably from 0.5-fold by mass to 80-fold by mass, and more preferably from 5-fold by mass to 20-fold by mass, with respect to the concentrate. Within this range, at a time of isolation of a desired product, the amount of the alcohol evaporated can be reduced, and further, a sufficient amount of the alkali metal salt can be precipitated.

An insoluble material in the alcohol solution is the alkali metal sulphate, which may be separated out and removed by filtration or decantation. The temperature for filtration or decantation is preferably from 0° C. to 50° C., and more preferably from 1° C. to 25° C. Within this range, it is possible to precipitate only the alkali metal sulphate selectively, and thus, the yield of a desired product is high.

In the case where the alkali metal sulphate is incorporated into the alcohol solution obtained as described above, the obtained alcohol solution may be concentrated and be dissolved in an alcohol again to repeat the operation for separation and removal the alkali metal sulphate.

By evaporating the alcohol from the alcohol solution, it is possible to acquire a mixture of 10% by mole or less of a (6-methyl-3-sulphonatophenyl)(2-methylphenyl)phenylphosphine alkali metal salt, and 90% by mole or more of a bis(6-methyl-3-sulphonatophenyl)phenylphosphine dialkali metal salt, as a solid. This mixture will be hereinafter abbreviated as a mixture of alkali metal salts.

This mixture of alkali metal salts is preferably formed of 5% by mole or less of a (6-methyl-3-sulphonatophenyl)(2-methylphenyl)phenylphosphine alkali metal salt, and 95% by mole or more of a bis(6-methyl-3-sulphonatophenyl)phenylphosphine dialkali metal salt.

In order to increase the content of the bis(6-methyl-3-sulphonatophenyl)phenylphosphine dialkali metal salt in the mixture of alkali metal salts, column chromatography using a mixed solvent including water, tetrahydrofuran, and the like as a mobile phase, which is passed through a column packed with silica gel, can be used. Alternatively, a method in which an aqueous solution of a mixture of alkali metal salts is prepared and washed with an organic solvent such as 2-butanone can also be used.

[3. Ion Exchange Step]

By reacting the mixture of alkali metal salts obtained in the neutralization step with a strongly acidic cation exchange resin, bis(6-methyl-3-sulphophenyl)phenylphosphine can be derived from the bis(6-methyl-3-sulphonatophenyl)phenylphosphine dialkali metal salt.

According to the investigations of the present inventors, in a known method including reacting a triarylphosphine in which a counter-cation of a sulpho group is an alkali metal with a tertiary amine and carbon dioxide in the presence of an alcohol solvent, and a known method including reacting a triarylphosphine in which a counter-cation of a sulpho group is an alkali metal with a protonic acid in a solvent such as an acyclic ketone, the yield of a desired product is lowered in any case. Therefore, it is crucial to use a strongly acidic ion exchange resin, and according to the method, the yield of a desired product is increased.

It is also possible to bring an alcohol solution of the mixture of alkali metal salts as it is into contact with a strongly acidic cation exchange resin, but since the solubility of the mixture of alkali metal salts in an alcohol is lower than that in water, it is preferable to bring the mixture of alkali metal salts from an aqueous solution into contact with a strongly acidic cation exchange resin to undergo a reaction.

By using a strongly acidic cation exchange resin as a cation exchange resin, the alkali metal ions can be sufficiently converted to protons even with a small amount of the ion exchange resin.

As the strongly acidic cation exchange resin, those in which a sulpho group is introduced to a copolymer of styrene and divinylbenzene, a copolymer of perfluorosulphonic acid and tetra fluoroethylene, and the like can be preferably used.

Examples of the strongly acidic cation exchange resin include those which are non-aqueous and aqueous, either of which may be used. According to the type of a substrate, a macroporous type substrate, a gel type substrate, and the like can be mentioned, either of which may be used. As the strongly acidic cation exchange resin, those in which the counterion of a sulpho group contained in the resin is a proton or a sodium ion is generally known. In the case where the counterion is a sodium ion, the sodium ion is converted to a proton by carrying out a pre-treatment with a protonic acid such as hydrochloric acid and sulphuric acid, then the pretreated resin is used. In the case of a resin in which the counterion is a proton, it can be used without a pre-treatment.

The strongly acidic cation exchange resin may have a powder shape or particulate shape, but from the viewpoint of avoiding damage due to friction in the state of use, it is preferable to use a resin having a particulate shape. In the case of using a resin having a particulate shape, the average particle diameter is not particularly limited, and is preferably from 0.3 mm to 3 mm, and more preferably from 0.5 mm to 1.5 mm. When the average particle diameter is 0.3 mm or more, it is difficult for the resin to be incorporated into a product, whereas when the average particle diameter is 3 mm or less, a large contact area of the resin with the aqueous solution of the mixture of alkali metal salts can be maintained, and as a result, the amount of the strongly acidic cation exchange resin used can be reduced.

Examples of the strongly acidic cation exchange resin formed by introducing a sulpho group into a copolymer of styrene and divinylbenzene, which satisfies the above, include Amberlyst 15, Amberlyst 16, Amberlyst 31, Amberlyst 32, and Amberlyst 35, all manufactured by Rohm and Haas Company [in which Amberlyst is a registered trademark], Dowex 50W, Dowex 88, and Dowex G-26 [in which Dowex is a registered trademark], all manufactured by Dow Chemical Company, and Diaion SK104, Diaion SK1B, Diaion PK212, Diaion PK216, and Diaion PK228 [in which Diaion is a registered trademark], all manufactured by Mitsubishi Chemical Corporation.

Examples of the strongly acidic cation exchange resin as a copolymer of perfluorosulphonic acid and tetrafluoroethylene include Nafion SAC-13 and Nafion NR-50 [in which Nafion is a registered trademark], both manufactured by E. I. du Pont de Nemours and Company.

The strongly acidic cation exchange resins may be used alone or in combination of two or more kinds thereof.

The ion exchange step can be carried out in either a flow mode or a batch mode. In the case of carrying out the step in a flow mode using a column, a fixed bed reactor, or the like, damage due to the friction of the strongly acidic cation exchange resin can be inhibited, and further, there is an effect that the equilibrium reaction is biased, whereby the amount of the strongly acidic cation exchange resin used can be reduced.

From the view point of making the flow of the aqueous solution uniform, it is preferable that the reactor has a tubular structure. The tube diameter is not particularly limited, but it is preferably from 50 mm to 500 mm from the viewpoint of making the exchange operation of the strongly acidic cation exchange resin convenient. The length and number of the reactor tube as a reactor are not particularly limited, but are preferably appropriately set with the viewpoint of the production cost, strongly acidic cation exchange resin and the like, which the resin is required to achieve a desired production capacity of the reactor.

In addition, the laminar flow may be in a down-flow mode for supplying the aqueous solution from the top of a reactor or an upflow mode for supplying from the bottom of a reactor when the reactor is a fixed bed reactor.

The concentration of the mixture of alkali metal salts in the aqueous solution of the mixture of alkali metal salts is preferably from 1% by mass to 30% by mass, and more preferably from 5% by mass to 20% by mass. Within these ranges, it is possible to substitute 99% by mole or more of the alkali metals ion into a protons even with a small amount of water used.

The temperature of the aqueous solution of the mixture of alkali metal salts is preferably from 10° C. to 120° C. If the temperature is 10° C. or higher, there is no reduction in the ion exchange rate and the increase in the amount of the strongly acidic cation exchange resin used can be avoided. Further, if the temperature is 120° C. or lower, the pores of the resin can be inhibited from being closed by the deformation of the ion exchange resin, and in addition, the reduction in the ion exchange rate can be inhibited.

The of the strongly acidic cation exchange resin used preferably corresponds to 1.5 times or more the theoretical ion-exchangeable amount which is calculated from the amount of the alkali metal ions to be preliminarily exchanged. By this, it is possible to exchange 99% by mole or more of the alkali metal ions included in the mixture of alkali metal salts with protons. In addition, in the case where a higher ion exchange rate is desired, the alkali metal ions may undergo a reaction repeatedly with the strongly acidic cation exchange resin.

The flow rate of the aqueous solution of the mixture of alkali metal salts is not particularly limited, but the liquid hourly space velocity (LHSV), a value obtained by dividing a volume velocity (m$^3$/hr) of the aqueous solution supplied by a volume (m$^3$) of a resin layer including the strongly acidic cation exchange resin, is preferably from 5 hr$^{-1}$ to 30 hr$^{-1}$, and more preferably from 10 hr$^{-1}$ to 20 hr$^{-1}$. Within this range, the ion exchange efficiency is high.

By evaporating water from an aqueous solution which has been brought into contact with the strongly acidic cation exchange resin, it is possible to acquire a mixture of 10% by mole or less of (6-methyl-3-sulphophenyl)(2-methylphenyl)phenylphosphine, and 90% by mole or more of bis(6-methyl-3-sulphophenyl)phenylphosphine, as a solid. This mixture will be hereinafter abbreviated as an ion exchanged mixture.

The ion exchanged mixture is preferably formed of 5% by mole or less of (6-methyl-3-sulphophenyl)(2-methylphenyl)phenylphosine, and 95% by mole or more of bis(6-methyl-3-sulphophenyl)phenylphosphine.

[4. Ammonium Salt Forming Step]

It is possible to derive a corresponding ammonium salt by allowing a sulpho group included in the ion exchanged mixture obtained in the ion exchange step to undergo a reaction with the same number of moles of a tertiary amine.

It is preferable that the ion exchanged mixture is dissolved in water, and from the viewpoint of reducing the amount of the solvent evaporated, the ion exchanged mixture is preferably used as an aqueous solution including 3% by mass to 25% by mass of the ion exchanged mixture.

The appropriate amount of the tertiary amine can be confirmed by potentiometric titration. In the case of adding excess tertiary amine, the excess tertiary amine may be evaporated.

The amount of tertiary amine used is preferably 1-fold by mole to 2-fold by mole, more preferably 1.1-fold by mole to 2-fold by mole, and still more preferably 1.1-fold by mole to 1.5-fold by mole that of the sulpho groups included in the ion exchanged mixture.

By concentrating a solution obtained by reacting the ion exchanged mixture with the tertiary amine to dryness, a desired product as a solid can be isolated, and by evaporating a part of the water, a concentrated aqueous solution can be acquired or the solution may be used as it is.

By directly adding the tertiary amine to the aqueous solution of the ion exchanged mixture, and sufficiently mixing them at 10° C. to 30° C. over 0.5 hours to 3 hours, the reaction with the corresponding ammonium sufficiently proceeds.

Furthermore, as the tertiary amine, a tertiary amine having a total of 3 to 27 carbon atoms in alkyl groups bonded to one nitrogen atom is used.

Examples of the tertiary amine include trimethylamine, triethylamine, tripropylamine, triisopropylamine, tributylamine, triisobutylamine, tri-s-butylamine, tri-t-butylamine, tripentylamine, triisopentylamine, trineopentylamine, trihexylamine, triheptylamine, trioctylamine, triphenylamine, tribenzylamine, N,N-dimethylethylamine, N,N-dimethylpropylamine, N,N-dimethylisopropylamine, N,N-dimethylbutylamine, N,N-dimethylisobutylamine, N,N-dimethyl-s-butylamine, N,N-dimethyl-t-butylamine, N,N-dimethylpentylamine, N,N-dimethylisopentylamine, N,N-dimethylneopentylamine, N,N-dimethylhexylamine, N,N-dimethylheptylamine, N,N-dimethyloctylamine, N,N-dimethylnonylamine, N,N-dimethyldecylamine, N,N-dimethylundecylamine, N,N-dimethyldodecylamine, N,N-dimethylphenylamine, N,N-dimethylbenzylamine, N,N-diethylmonomethylamine, N,N-dipropylmonomethylamine, N,N-diisopropylmonomethylamine, N,N-dibutylmonomethylamine, N,N-diisobutylmonomethylamine, N,N-di-s-butylmonomethylamine, N,N-di-t-butylmonomethylamine, N,N-dipentylmonomethylamine, N,N-diisopentylmonomethylamine, N,N-dineopentylmonomethylamine, N,N-dihexylmonomethylamine, N,N-diheptylmonomethylamine, N,N-dioctylmonomethylamine, N,N-dinonylmonomethylamine, N,N-didecylmonomethylamine, N,N-diundecylmonomethylamine, N,N-didodecylmonomethylamine, N,N-diphenylmonomethylamine, N,N-dibenzylmonomethylamine, N,N-dipropylmonoethylamine, N,N-diisopropylmonoethylamine, N,N-dibutylmonoethylamine, N,N-diisobutylmonoethylamine, N,N-di-s-butylmonoethylamine, N,N-di-t-butylmonoethylamine, N,N-dipentylmonoethylamine, N,N-diisopentylmonoethylamine, N,N-dineopentylmonoethylamine, N,N-dihexylmonoethylamine, N,N-diheptylmonoethylamine, N,N-dioctylmonoethylamine, N,N-dinonylmonoethylamine, N,N-didecylmonoethylamine, N,N-diundecylmonoethylamine, N,N-didodecylmonoethylamine, N,N-diphenylmonoethylamine, N,N-dibenzylmonoethylamine, and trinonylamine. These may be used alone or as a mixture of two or more kinds thereof.

The total number of carbon atoms in groups bonded to one nitrogen atom is preferably from 3 to 24, more preferably from 5 to 24, still more preferably from 5 to 10, and particularly preferably from 5 to 7. Further, as the group bonded to one nitrogen atom, an alkyl group, an aryl group, and an aryl-substituted alkyl group are preferred, and an alkyl group is more preferred.

Among those, as the tertiary amine, triethylamine, N,N-dimethylisopropylamine, and trioctylamine are preferred, and from the viewpoints of easy availability and production cost, triethylamine and N,N-dimethylisopropylamine are more preferred.

By evaporating water from the reaction mixed solution after completion of the reaction, it is possible to acquire a mixture of 10% by mole or less of a (6-methyl-3-sulphonatophenyl)(2-methylphenyl)phenylphosphine ammonium salt, and 90% by mole or more of a bis(6-methyl-3-sulphonatophenyl)phenylphosphine diammonium salt, as a solid. This mixture will be hereinafter abbreviated as a mixture of ammonium salts.

The mixture of ammonium salts is preferably formed of 5% by mole or less of a (6-methyl-3-sulphonatophenyl)(2-methylphenyl)phenylphosphine ammonium salt, and 95% by mole or more of a bis(6-methyl-3-sulphonatophenyl)phenylphosphine diammonium salt.

In order to increase the content of the bis(6-methyl-3-sulphonatophenyl)phenylphosphine diammonium salt in the mixture of ammonium salts, column chromatography using a mixed solvent including water, tetrahydrofuran, and the like as a mobile phase, which is passed through a column packed with silica gel, can be used. Alternatively, a method in which an aqueous solution of an mixture of alkali metal salts is prepared and washed with an organic solvent such as 2-butanone can also be used.

A palladium catalyst comprised of the bis(6-methyl-3-sulphonatophenyl)phenylphosphine diammonium salt obtained as above, or a mixture containing the same, and a palladium compound is excellent as a catalyst for a telomerization reaction. Examples of the telomerization reaction include a reaction in which butadiene is reacted with water in the presence of a palladium catalyst, a tertiary amine, and carbon dioxide to obtain 2,7-octadien-1-ol. In the telomerization reaction, the selectivity for 2,7-octadien-1-ol is improved and the recovery of the palladium catalyst is high, and therefore, the industrial availability is very high.

Furthermore, preferred examples of the palladium compound include 0-valent palladium compounds such as bis(t-butylisonitrile)palladium(0), bis(t-amlisonitrile)palladium (0), bis(cyclohexylisonitrile)palladium(0), bis (phenylisonitrile)palladium(0), bis(p-tolylisonitrile) palladium(0), bis(2,6-dimethylphenylisonitrile)palladium (0), tris(dibenzylideneacetone) dipalladium(0), (1,5-cyclooctadiene)(maleic anhydride)palladium(0), bis (norbornene)(maleic anhydride)palladium(0), bis(maleic anhydride)(norbornene)palladium(0), (dibenzylideneacetone)(bipyridyl)palladium(0), (p-benzoquinone)(o-phenanthroline)palladium(0), tetrakis(triphenylphosphine)palladium(0), tris(triphenylphosphine)palladium(0), bis (tritolylphosphine)palladium(0), bis(trixylylphosphine) palladium(0), bis(trimesitylphosphine)palladium(0), bis (tritetramethylphenyl)palladium(0), and bis (trimethylmethoxyphenylphosphine)palladium(0); and divalent palladium compounds such as palladium (II) chloride, palladium (II) nitrate, tetraammine dichloropalladium (II), disodium tetrachloropalladium (II), palladium (II) acetate, palladium (II) benzoate, palladium (II) α-picolinate, bis(acetylacetone) palladium (II), bis(8-oxyquinoline) palladium (II), bis(allyl) palladium (II), (η-allyl) (η-cyclopentadienyl)palladium (II), (η-cyclopentadienyl)(1,5-cyclooctadiene)palladium (II) tetrafluoroborate, bis(benzonitrile) palladium (II) acetate, di-μ-chlorodichlorobis (triphenylphosphine)dipalladium (II), bis(tri-n-butylphosphine)palladium (II) acetate, and 2,2-bipyridyl palladium (II) acetate.

Furthermore, in the case where the telomerization reaction is carried out industrially, a step of mixing the telomerization reaction liquid obtained in the telomerization reaction step with an organic solvent having a dielectric constant of 2 to 18 at 25° C., followed by performing phase separation in the presence of carbon dioxide, thereby obtaining 2,7-octadien-1-ol from an organic phase (product separation step), and a step of recovering an aqueous phase including the palladium catalyst with high efficiency (catalyst recovery step) are preferably carried out. At this time, in the case of using the bis(6-methyl-3-sulphonatophenyl)phenylphosphine diammonium salt or the mixture containing the same, of the present invention, as a raw material for a palladium catalyst, the selectivity for a desired product and the recovery of the palladium catalyst are higher, as compared with other palladium catalysts, and therefore, the production cost is reduced, which is thus preferable.

Furthermore, examples of the organic solvent having a dielectric constant of 2 to 18 at 25° C. include n-dodecane, cyclohexane, 1,4-dioxane, benzene, p-xylene, m-xylene, toluene, dibutyl ether, diisopropyl ether, propanenitrile, ethylphenyl ether, diethyl ether, methyl-t-butyl ether, cyclopentylmethyl ether, fluorobenzene, 2-methyltetrahydrofuran, tetrahydrofuran, 2-heptanone, 4-methyl-2-pentanone, cyclopentanone, 2-hexanone, 2-pentanone, cyclohexanone, 3-pentanone, and acetophenone. Further, the dielectric constant of the organic solvent is preferably from 3 to 10.

EXAMPLES

Hereinafter, the present invention will be described in more detail with reference to Examples, but the present invention is not limited to such Examples in any case.

Hereinafter, in the production of various water-soluble triarylphosphines, the production was carried out at room temperature, at normal pressure, or under a nitrogen atmosphere unless otherwise specified, and as the solvent, those which had been purged with nitrogen in advance were used.

In addition, the water-soluble triarylphosphine obtained by sulphonating triarylphosphine may be a mixture of those in which the number of sulpho groups introduced is 1 to 3 in some case, and may further include oxides formed by oxidation of the phosphorus.

The composition ratios (mass ratios) thereof in the water-soluble triarylphosphine were quantified from peak areas of $^{31}P$ obtained by measurement using a nuclear magnetic resonance apparatus "AVANCE III 400 USPlus" (manufactured by Bruker BioSpin K. K.) with a dimethylsulphoxide-$d_6$ (hereinafter referred to as DMSO-$d_6$) solution prepared such that the concentration of the produced water-soluble triarylphosphine is 0.05 mol/L. The chemical shift of $^{31}P$ in this case is a value at 305 K in the case where the chemical shift of the DMSO-$d_6$ solution prepared to a concentration of the phosphoric acid of 0.05 mol/L is set to 0 ppm.

Furthermore, the structure of the water-soluble triarylphosphine is determined from the chemical shifts and the peak areas of $^{31}P$ and $^1H$ obtained by measurement using a nuclear magnetic resonance apparatus "AVANCEIII 600 USPlus" (manufactured by Bruker BioSpin K. K.) with a deuterium oxide solution prepared to have a concentration of 10 mmol/L. The chemical shift of $^{31}P$ in this case is a value at 300 K in the case where the chemical shift of a deuterium oxide solution prepared to have a concentration of the phosphoric acid of 10 mmol/L is set to 0 ppm. The chemical shift of $^1H$ in this case is a value at 300 K in the case where the chemical shift of a deuterium oxide solution prepared to have a concentration of trimethylsilylpropanoic acid-$d_4$ (hereinafter abbreviated as TSP) of 5 mmol/L is set to 0 ppm.

Sodium ions were quantified using Ion Chromatography "ICS-1500 Type" (manufactured by Nippon Dionex K. K.).

For the operation for purifying a desired product, a high performance liquid chromatographic system (manufactured by Nihon Waters K.K., DELTA 600 MULTI-SOLVENT Systems, 2998 Photodiode array detector, a column heater, a chromatography data software Empower1) was used. Further, as a reversed phase chromatography column, a "TSKgel ODS-80Ts" (particle diameter of 5 μm, inner diameter of 20 mm, and length of 250 mm) manufactured by Tosoh Corporation, was used.

Production of Water-Soluble Triarylphosphine

Example 1

Production of Bis(6-methyl-3-sulphophenyl)phenylphosphine

A sulphonation reaction was carried out in a batch mode. 10 g of concentrated sulphuric acid was placed in a 4-neck flask having an inner capacity of 100 ml, equipped with a thermometer, a stirring device, a dropping funnel, and a nitrogen gas line. The concentrated sulphuric acid was stirred, and 10.00 g (34.44 mmol in terms of phosphorous atoms) of bis(2-methylphenyl)phenylphosphine (hereinafter abbreviated as DOTPP) was introduced thereto over 0.5 hours so as to maintain the liquid temperature at 30° C. to 35° C., 35.3 g (132.3 mmol in terms of sulphur trioxide) of fuming sulphuric acid containing 30% by mass of sulphur trioxide was added dropwise thereto over 2 hours from the dropping funnel so as to maintain the same temperature. After completion of dropwise addition, stirring was continuously performed at a liquid temperature of 30° C. to 35° C. for 8 hours and at 20° C. to 25° C. over 15 hours.

The liquid temperature was controlled such that it was in a range of 20° C. to 30° C., and the sulphonation reaction liquid was diluted with 90 g of ion-exchanged water. The aqueous phase was adjusted to have pH 8 to 9 by adding 113 g of an aqueous 30%-by-mass sodium hydroxide solution, and subsequently, 39.0 g of an aqueous 5%-by-mass sodium hydroxide solution. This neutralized liquid was concentrated to dryness in the range of 38° C. to 70° C. and 4 kPa to 56 kPa, and 720 g of methanol was added to the obtained concentrated solution, followed by suction-filtering, thereby obtaining a filtrate. This filtrate was concentrated to dryness in the range of 15° C. to 50° C. and 4 kPa to 56 kPa, thereby acquiring 16.84 g of a white solid (hereinafter abbreviated as an acquisition 1).

A column made of glass (31 mm in diameter and 340 mm in height), packed with 100 g of a strongly acidic cation exchange resin, Dowex G-26, was prepared. 168.4 g (16.84 g in terms of the acquisition 1 and 34.21 mmol in terms of phosphorous atoms) of an aqueous solution including 10% by mass of the acquisition 1 was allowed to pass from the upper part of the column at a linear velocity of 9.3 m/hr to 12.5 m/hr. This obtained liquid was concentrated to dryness in the range of 15° C., and 4 kPa to 56 kPa to acquire 14.76 g of a white solid (hereinafter abbreviated as an acquisition 2).

According to the atomic absorption analysis of the acquisition 2, the sodium content included in the acquisition 2 was 294 ppm or less in terms of sodium atoms. From the viewpoint that the number of sulpho groups contained in 10.0 g of the acquisition 2 was 44.11 mmol and the content of the sodium atoms was 0.13 mmol, 99.71% by mole or more of the sulphonate groups had been converted to sulpho groups.

The acquisition 2 was a mixture containing 0.25 g (0.68 mmol, 2.08% by mole) of (6-methyl-3-sulphophenyl)(2-methylphenyl)phenylphosphine, and 14.51 g (32.20 mmol, 97.92% by mole) of bis(6-methyl-3-sulphophenyl)phenylphosphine. From the viewpoint that 14.76 g (32.89 mmol in terms of phosphorous atoms) of the acquisition 2 could be acquired by using 10.00 g (34.44 mmol in terms of phosphorous atoms) of DOTPP, the yield based on the phosphorous atoms was 95.5%.

Example 2

Purification of Bis(6-methyl-3-sulphophenyl)phenylphosphine

Using a high performance liquid chromatographic system equipped with a reversed phase chromatography column, a mixed liquid including 70% by mass of water and 30% by mass of acetonitrile as a mobile phase was passed through the system at 5.0 mL/minute in the state where a column oven temperature was controlled such that it was 40° C. 1 g of an aqueous solution including 1% by mass of the acquisition 2 of Example 1 was prepared, and injected. The photodiode array detector was set to 275 nm and a distillate with a retention time of 15 minutes to 30 minutes was recovered. This operation was repeated 10 times. The collected distillate was concentrated to dryness in the range of 35° C. to 70° C. and 4 kPa to 56 kPa to acquire 45.5 mg of bis(6-methyl-3-sulphophenyl)phenylphosphine as a white solid.

$^{31}$P-NMR (600 MHz, 300 K, deuterium oxide, phosphoric acid, ppm) δ: −17.44 (s)

$^{1}$H-NMR (600 MHz, 300 K, deuterium oxide, TSP, ppm) δ: 2.34 (s, 6H), 7.24 (dd, 2.1 Hz, 1.7 Hz, 2H), 7.33 (t, 7.9 Hz, 2H), 7.37 to 7.46 (m, 4H), 7.49 (t, 7.2 Hz, 1H), 7.79 dd, 1.3 Hz, 2H)

From the viewpoint that 45.5 mg (0.101 mmol in terms of phosphorous atoms) of a desired product could be acquired by using 100.0 mg (0.223 mmol in terms of phosphorous atoms) of the acquisition 2, the yield based on the phosphorous atoms in the purification was 45.3%.

Example 3

Production of Bis(6-methyl-3-sulphonatophenyl)phenylphosphine Di(triethylammonium) Salt An aqueous solution including the acquisition 2 was acquired in the same manner as in Example 1, and 7.5 g (74.3 mmol) of triethylamine was added thereto, followed by stirring the mixture in the range of 20° C. to 30° C. over 1 hour, to carry out a reaction. Thereafter, the reaction liquid was concentrated to dryness in the range of 35° C. to 70° C. and 4 kPa to 56 kPa, thereby acquiring 21.21 g of a pale yellow solid.

$^{31}$P-NMR (400 MHz, 305 K, DMSO-$d_6$, phosphoric acid, ppm) δ: a (6-methyl-3-sulphonatophenyl)(2-methylphenyl)phenylphosphine triethylammonium salt showed a peak at −19.81 (s), and a bis(6-methyl-3-sulphonatophenyl)phenylphosphine di(triethylammonium) salt showed a peak at −17.02 (s).

The acquisition was mixture containing 0.32 g (0.69 mmol, 2.10% by mole) of a (6-methyl-3-sulphonatophenyl)(2-methylphenyl)phenylphosphine triethylammonium salt, and 20.89 g (31.99 mmol, 97.90% by mole) of a bis(6-methyl-3-sulphonatophenyl)phenylphosphine di(triethylammonium salt. From the viewpoint that 21.21 g (32.68 mmol in terms of phosphorous atoms) of a desired product could be acquired from 10.00 g (34.44 mmol in terms of phosphorous atoms) of DOTPP, the yield based on the phosphorous atoms was 94.0%.

Example 4

Production of Bis(6-methyl-3-sulphonatophenyl)phenylphosphine Di(tri-n-octylammonium) Salt An aqueous solution including the acquisition 2 was acquired in the same manner as in Example 1, and 26.28 g (74.3 mmol) of tri-n-octylamine was added thereto, followed by stirring the mixture in the range of 20° C. to 30° C. over 1 hour, to carry out a reaction. Thereafter, the reaction liquid was concentrated to dryness in the range of 35° C. to 70° C. and 4 kPa to 56 kPa, thereby acquiring 37.18 g of a pale yellow solid.

$^{31}$P-NMR (400 MHz, 305 K, DMSO-$d_6$, phosphoric acid, ppm) δ: a (6-methyl-3-sulphonatophenyl)(2-methylphenyl)phenylphosphine tri-n-octyl ammoniumammonium salt showed a peak at −20.39 (s), and a bis(6-methyl-3-sulphonatophenyl)phenylphosphine di(tri-n-octylammonium) salt showed a peak at −17.20 (s).

The acquisition was a mixture containing 0.50 g (0.70 mmol, 2.15% by mole) of a (6-methyl-3-sulphonatophenyl)

(2-methylphenyl)phenylphosphine tri-n-octylammonium salt, and 36.68 g (31.68 mmol, 97.85% by mole) of a bis(6-methyl-3-sulphonatophenyl)phenylphosphine di(tri-n-octylammonium) salt. From the viewpoint that 37.18 g (32.37 mmol in terms of phosphorous atoms) of a desired product could be acquired from 10.00 g (34.44 mmol in terms of phosphorous atoms) of DOTPP, the yield based on the phosphorous atoms was 94.0%.

<Telomerization Reaction>

Hereinafter, it is shown that the water-soluble triarylphosphine of the present invention is useful for a telomerization reaction with reference to Reference Examples. Further, the present invention is not limited to such Reference Examples in any case.

Moreover, the concentrations of the palladium compounds and the phosphorus compounds included in the aqueous phase acquired by an extraction operation were quantified by subjecting a wet decomposition product to analysis using a polarized Zeeman atomic absorption spectrophotometer "Z-5300 Type" (manufactured by Hitachi, Ltd.).

In addition, organic materials such as a tertiary amine and 2,7-octadien-1-ol included in the telomerization reaction liquid or the aqueous phase including the palladium catalyst were analyzed and quantified by gas chromatography under the following measurement conditions.

(Analysis Conditions for Gas Chromatography)

Apparatus: GC-14 A (Manufactured by Shimadzu Corporation)

Column used: G-300 (1.2 mm in internal diameter×20 m in length, and a film thickness of 2 μm), (Materials) manufactured by Chemicals Evaluation, and Research Institute, Japan Analysis conditions: an inlet temperature of 220° C., and a detector temperature of 220° C.

Sample injection amount: 0.4 μL

Carrier gas: helium (260 kPa) is flowed at 10 mL/minute.

Column temperature: maintained at 60° C. for 5 minutes-→raised at 10° C./minute→maintained at 220° C. for 9 minutes Detector: hydrogen flame ionization detector (FID)

Reference Example 1

The telomerization reaction was carried out in a batch mode. A 3 L autoclave equipped with an SUS316 electromagnetic induction stirring device including a 96 mL pressure container made of glass, for pumping a palladium catalyst, a 96 mL pressure container made of glass, for pumping a solvent, and a sampling port was used as a reactor. Further, the reaction was carried out at a stirring rotation speed of 500 rpm, and from the viewpoint that the reaction results at this time were not different from those at 1,000 rpm, a sufficient stirring state could be achieved.

17.69 g of a tetrahydrofuran solution including 94.74 mg (0.422 mmol in terms of palladium atoms) of palladium (II) acetate, and then 21.46 g of an aqueous solution including 1.370 g (2.109 mmol in terms of trivalent phosphorous atoms) of the phosphorous compound obtained in Example 3 were introduced into a pressure container made of glass and stirred for 60 minutes to prepare a palladium catalyst liquid.

30.06 g of distilled water, 80.10 g of triethylamine, 97.50 g of 2,7-octadien-1-ol, and 114.95 g (2.13 mol) of butadiene were put into the autoclave, followed by stirring at 500 rpm in a closed system and warming to 70° C. Thereafter, the palladium catalyst liquid was pumped from the pressure container made of glass through carbon dioxide within 10 seconds, while the total pressure was set to 1.2 MPa (gauge pressure). Further, a time point at which pumping of the palladium catalyst liquid was completed was defined as 0 hours at initiation of reaction.

In addition, the ratio of the trivalent phosphorus atoms to the palladium atoms at a time of preparation of a catalyst was 5.00, and in the telomerization reaction, the amount of the palladium atoms with respect to 1 mol of butadiene was 0.198 mmol, the mass ratio of triethylamine to water was 1.55, and the mass ratio of a mixture of butadiene and 2,7-octadien-1-ol to water was 4.12.

For the telomerization reaction liquid after a predetermined reaction time, the product was quantified by gas chromatography analysis.

The conversion of the butadiene was calculated by the following Equation 1. Further, the respective units in the equations are mol.

Butadiene conversion (%)=100×{1−(Amount of butadiene in reaction liquid/Amount of butadiene introduced)}  [Equation 1]

Examples of the respective products include 2,7-octadien-1-ol, 1,7-octadien-3-ol, 1,3,6-octatriene, 1,3,7-octatriene, 2,4,6-octatriene, and 4-vinylcyclohexene. However, 1,3,6-octatriene, 1,3,7-octatriene, and 2,4,6-octatriene are collectively referred to as octatrienes. The selectivities of the respective products were calculated by the following Equation 2. Further, the respective units in the equations are mol.

Selectivity for each product (%)=50×(Amount of each product in reaction liquid/Amount of butadiene reacted)  [Equation 2]

The selectivities for high-boiling-point products which could not be sufficiently quantified by gas chromatography were calculated by the following Equation 3. Further, the respective units in the equations are mol.

Selectivity for high-boiling-point products (%)=100−(Total sum of selectivities of the respective products, calculated by Equation 2)  [Equation 3]

After 8 hours of the reaction, the butadiene conversion was 77.9%, the selectivity for 2,7-octadien-1-ol was 88.7%, the selectivity for 1,7-octadien-3-ol was 7.4%, the selectivity for octatrienes was 2.1%, and the selectivity for the high-boiling-point products was 1.8%. Further, the selectivity for 4-vinylcyclohexene was 0.01% or less.

The autoclave was cooled to 25° C., and a reaction consumption-equivalent amount of water and 330.23 g (a volume at 25° C. of 463.2 mL) of diethyl ether were pumped through carbon dioxide, using a 96 mL pressure container made of glass, for pumping a solvent. The mixture was stirred for 1 hour while being pressurized to a total pressure of 3 MPa (gauge pressure) with carbon dioxide. This mixed liquid was transferred to a pressure container equipped with a glass window, which had been pressurized to 3 MPa (gauge pressure) with carbon dioxide using a pump, to carry out phase separation. The aqueous phase was suitably recovered into a pressure container made of glass, which had been pressurized to 1 MPa (gauge pressure) with carbon dioxide, connected to a pressure container equipped with a glass window. The pressure container made of glass was taken out, separated, and opened at normal pressure, and the weight of the aqueous phase was measured, while the acquired aqueous phase was used for various types of analysis.

In addition, the mass ratio of diethyl ether to the telomerization reaction liquid was 0.84.

The content of palladium included in the aqueous phase was calculated from the concentration of palladium as demonstrated by the analysis with a polarized Zeeman atomic absorption spectrophotometer using a wet decomposition product of the aqueous phase and the weight of the recovered aqueous phase. The recovery of the palladium atoms was calculated by the following Equation 4. Further, the units of the respective amounts in the equation are mol.

Recovery of palladium atoms (%)=(Amount of palladium in aqueous phase/Amount of palladium introduced)×100  [Equation 4]

The content of phosphorous included in the aqueous phase was calculated from the concentration of phosphorous as demonstrated by the analysis with a polarized Zeeman atomic absorption spectrophotometer using a wet decomposition product of the aqueous phase and the weight of the recovered aqueous phase. The recovery of the water-soluble triarylphosphine was calculated by the following Equation 5. Further, the units of the respective amounts in the equation are mol.

Recovery of water-soluble triarylphosphine (%)=100×(Amount of phosphorous atoms in aqueous phase/Amount of phosphorous atoms introduced)  [Equation 5]

The tertiary amine included in the aqueous phase was quantified by analyzing the aqueous phase using gas chromatography. The recovery of the tertiary amine was calculated by the following Equation 6. Further, the units of the respective amounts in the equations are mol.

Recovery of tertiary amine (%)=100×(Amount of tertiary amine in aqueous phase/Amount of tertiary amine introduced)  [Equation 6]

The recovery of the palladium atoms into the aqueous phase was 91.3%, the recovery of phosphorous atoms was 90.9%, and the recovery of triethylamine was 83.0%. Further, the amount of diethyl ether incorporated into the aqueous phase was 0.1% by mass or less.

Reference Example 2 (Comparative)

The same operation as in Reference Example 1 except that 2.120 g (2.120 mmol in terms of trivalent phosphorous atoms) of a diphenyl(3-sulphonatophenyl)phosphine triethylammonium salt (with the provision that it included 4.40% by mole of oxides) was used instead of the phosphorous compound obtained in Example 3 was carried out. Further, the ratio of the trivalent phosphorous atoms to the palladium atoms at a time of preparation of the catalyst was 5.02.

After 4 hours of the reaction, the butadiene conversion was 77.6%, the selectivity for 2,7-octadien-1-ol was 88.2%, the selectivity for 1,7-octadien-3-ol was 5.1%, the selectivity for octatrienes was 5.1%, and the selectivity for the high-boiling-point products was 1.6%. Further, the selectivity for 4-vinylcyclohexene was 0.01% or less.

The recovery of the palladium atoms into the aqueous phase was 28.2%, the recovery of phosphorous atoms was 48.8%, and the recovery of triethylamine was 65.5%. Further, the amount of diethyl ether incorporated into the aqueous phase was 0.1% by mass or less.

Reference Example 3 (Comparative)

The same operation as in Reference Example 1 except that 1.015 g (2.113 mmol in terms of trivalent phosphorous atoms) of a diphenyl(6-methyl-3-sulphonatophenyl)phosphine triethylammonium salt (with the provision that it included 4.58% by mole of oxides) was used instead of the phosphorous compound obtained in Example 3 was carried out. Further, the ratio of the trivalent phosphorous atoms to the palladium atoms at a time of preparation of the catalyst was 5.01.

After 4 hours of the reaction, the butadiene conversion was 85.0%, the selectivity for 2,7-octadien-1-ol was 88.8%, the selectivity for 1,7-octadien-3-ol was 5.0%, the selectivity for octatrienes was 4.4%, and the selectivity for the high-boiling-point products was 1.8%. Further, the selectivity for 4-vinylcyclohexene was 0.01% or less.

The recovery of the palladium atoms into the aqueous phase was 12.0%, the recovery of phosphorous atoms was 28.3%, and the recovery of triethylamine was 76.5%. Further, the amount of diethyl ether incorporated into the aqueous phase was 0.1% by mass or less.

According to Example 1, it is apparent that a mixture of 5% by mole or less of (6-methyl-3-sulphophenyl)(2-methylphenyl)phenylphosine, and 95% by mole or more of bis(6-methyl-3-sulphophenyl)phenylphosphine can be acquired with high yield.

Furthermore, according to Example 2, it is apparent that bis(6-methyl-3-sulphophenyl)phenylphosphine can be isolated and purified by column chromatography.

According to Examples 3 and 4, it is apparent that a bis(6-methyl-3-sulphonatophenyl)phenylphosphine diammonium salt can be acquire with high yield by reacting bis(6-methyl-3-sulphophenyl)phenylphosphine with a tertiary amine having a total of 3 to 27 carbon atoms in groups bonded to one nitrogen atom.

According to Reference Examples 1 to 3, it is apparent that the bis(6-methyl-3-sulphonatophenyl)Phenylphosphine diammonium salt provided by the present invention can be obtained with higher selectivity in the telomerization reaction and the recovery of the palladium catalyst is higher, as compared with other water-soluble triarylphosphines, and therefore, it is useful when carrying out industrial telomerization reactions.

INDUSTRIAL APPLICABILITY

The bis(6-methyl-3-sulphonatophenyl)phenylphosphine diammonium salt obtained by using bis(6-methyl-3-sulphonatophenyl)phenylphosphine of the present invention is useful for a telomerization reaction of two molecules of an alkadiene such as butadiene with a nucleophilic reactant such as water.

The invention claimed is:

1. A method of performing a telomerization reaction, comprising reacting an alkadiene with water in the presence of a solid bis(6-methyl-3-sulphonatophenyl)phenylphosphine diammonium salt,
   wherein the solid bis(6-methyl-3-sulphonatophenyl)phenylphosphine diammonium salt is obtained by a process comprising: reacting bis(6-methyl-3-sulphophenyl)phenylphosphine with a tertiary amine comprising a total of 3 to 27 carbon atoms in groups bonded to one nitrogen atom.

2. The method of claim 1, wherein the tertiary amine is at least one selected from the group consisting of trimethylamine, triethylamine, tripropylamine, triisopropylamine, tributylamine, triisobutylamine, tri-s-butylamine, tri-t-butylamine, tripentylamine, triisopentylamine, trineopentylamine, trihexylamine, triheptylamine, trioctylamine, triphenylamine, tribenzylamine, N,N-dimethylethylamine, N,N-dimethylpropylamine, N,N-dimethylisopropylamine, N,N-dimethylbutylamine, N,N-dimethylisobutylamine, N,N-dimethyl-s-butylamine, N,N-dimethyl-t-butylamine, N,N-dimethylpentylamine, N,N-dimethylisopentylamine, N,N-dimethylneopentylamine, N,N-dimethylhexylamine, N,N-dimethylheptylamine, N,N-dimethyloctylamine, N,N-dimethylnonylamine, N,N-dimethyldecylamine, N,N-dimethylundecylamine, N,N-dimethyldodecylamine, N,N-dimethylphenylamine, N,N-dimethylbenzylamine N,N-diethylmonomethylamine, N,N-dipropylmonomethylamine, N,N-diisopropylmonomethylamine, N,N-dibutylmonomethylamine, N,N-diisobutylmonomethylamine, N,N-di-s-butylmonomethylamine, N,N-di-t-butylmonomethylamine, N,N-dipentylmonomethylamine, N,N-diisopentylmonomethylamine, N,N-dineopentylmonomethylamine, N,N-dihexylmonomethylamine, N,N-diheptylmonomethylamine, N,N-dioctylmonomethylamine, N,N-dinonylmonomethylamine, N,N-didecylmonomethylamine, N,N-diundecylmonomethylamine, N,N-didodecylmonomethylamine, N,N-diphenylmonomethylamine, N,N-dibenzylmonomethylamine, N,N-dipropylmonomethylamine, N,N-diisopropylmonoethylamine, N,N-dibutylmonoethylamine, N,N-diisobutylmonoethylamine, N,N-di-s-butylmonoethylamine, N,N-di-t-butylmonoethylamine, N,N-dipentylmonoethylamine, N,N-diisopentylmonoethylamine, N,N-dineopentylmonoethylamine, N,N-dihexylmonoethylamine, N,N-diheptylmonoethylamine, N,N-dioctylmonoethylamine, N,N-dinonylmonoethylamine, N,N-didecylmonoethylamine, N,N-diundecylmonoethylamine, N,N-didodecylmonoethylamine, N,N-diphenylmonoethylamine, N,N-dibenzylmonoethylamine, and trinonylamine.

3. The method of claim 1, wherein the tertiary amine comprises a total of 5 to 7 carbon atoms in groups bonded to one nitrogen atom.

4. The method of claim 1, wherein the tertiary amine is at least one selected from the group consisting of triethylamine and N,N-dimethylisopropylamine.

5. The method of claim 1, wherein the tertiary amine comprises triethylamine.

6. The method of claim 1, wherein the alkadiene comprises butadiene.

7. The method of claim 6, wherein the reacting of the alkadiene with water in the presence of the solid bis(6-methyl-3-sulphonatophenyl)phenylphosphine diammonium salt produces at least one product selected from the group consisting of 2,7-octadien-1-ol, 1,7-octadien-3-ol, 1,3,6-octatriene, 1,3,7-octatriene, 2,4,6-octatriene, and 4-vinylcyclohexene.

8. The method of claim 6, wherein the reacting of the alkadiene with water in the presence of the solid bis(6-methyl-3-sulphonatophenyl)phenylphosphine diammonium salt produces 2,7-octadien-1-ol.

9. The method of claim 1, wherein the reacting of the alkadiene with water in the presence of the solid bis(6-methyl-3-sulphonatophenyl)phenylphosphine diammonium salt produces at least one product selected from the group consisting of 2,7-octadien-1-ol, 1,7-octadien-3-ol, 1,3,6-octatriene, 1,3,7-octatriene, 2,4,6-octatriene, and 4-vinylcyclohexene.

10. The method of claim 1, wherein the reacting of the alkadiene with water in the presence of the solid bis(6-methyl-3-sulphonatophenyl)phenylphosphine diammonium salt produces 2,7-octadien-1-ol.

* * * * *